United States Patent [19]
Buess et al.

[11] Patent Number: 5,383,882
[45] Date of Patent: Jan. 24, 1995

[54] LIGATURE AND LIGATURE APPLYING ENDOSCOPIC INSTRUMENT

[75] Inventors: Gerhard Buess, Bebenhausen; Kirsten Huss, Ahrensburg; Sven Hempel, Kaltenkirchen; Thomas Schuldt, Hamburg, all of Germany

[73] Assignee: Ethicon, Inc., Somerville, N.J.

[21] Appl. No.: 97,357

[22] Filed: Jul. 26, 1993

[30] Foreign Application Priority Data

Aug. 28, 1992 [DE] Germany ............... 4228909

[51] Int. Cl.$^6$ .............................................. A61B 17/00
[52] U.S. Cl. ................................ 606/157; 606/151; 606/213
[58] Field of Search .............. 606/1, 151, 157, 213, 606/215–218

[56] References Cited

U.S. PATENT DOCUMENTS

| | | | |
|---|---|---|---|
| 3,570,497 | 3/1971 | Lemole | 606/151 |
| 3,577,601 | 5/1971 | Mariani | 606/151 |
| 3,926,193 | 12/1975 | Hasson | 606/218 |
| 4,592,355 | 6/1986 | Antebi | . |
| 4,730,615 | 3/1988 | Sutherland et al. | 606/215 |
| 4,813,416 | 3/1989 | Pollak et al. | 606/151 |
| 4,950,285 | 8/1990 | Wilk | 606/151 |
| 5,207,694 | 5/1993 | Broomé | 606/151 |

FOREIGN PATENT DOCUMENTS

WO90/06725  6/1990  WIPO ............... A61B 17/12

*Primary Examiner*—Stephen C. Pellegrino
*Assistant Examiner*—J. A. Schmidt
*Attorney, Agent, or Firm*—Paul A. Coletti

[57] ABSTRACT

An endoscopic instrument for the application of ligature binders and a ligature are described. A base body and an actuation part of a handle part are longitudinally displaceable relative to each other against an elastic force within a fixed range. Connected to the actuation part is an actuation rod at whose distal end a first ratchet heat is secured. A shaft, firmly connected to the base body, carries a second ratchet head at its distal end. With the help of the ratchet heads, which are matched to the toothed end zone of a ligature binder, a ligature can be drawn together. A ligature whose end zone has already been inserted into the endoscopic instrument prior to the operation can be brought into a closed shape with the help of a constricted zone in its binding part and of a longitudinal slot in its headpiece.

9 Claims, 5 Drawing Sheets

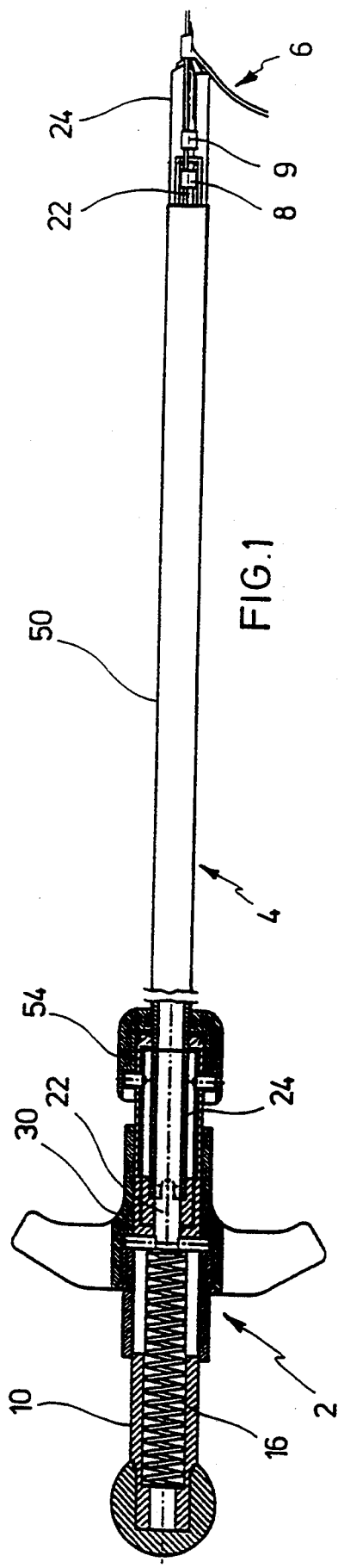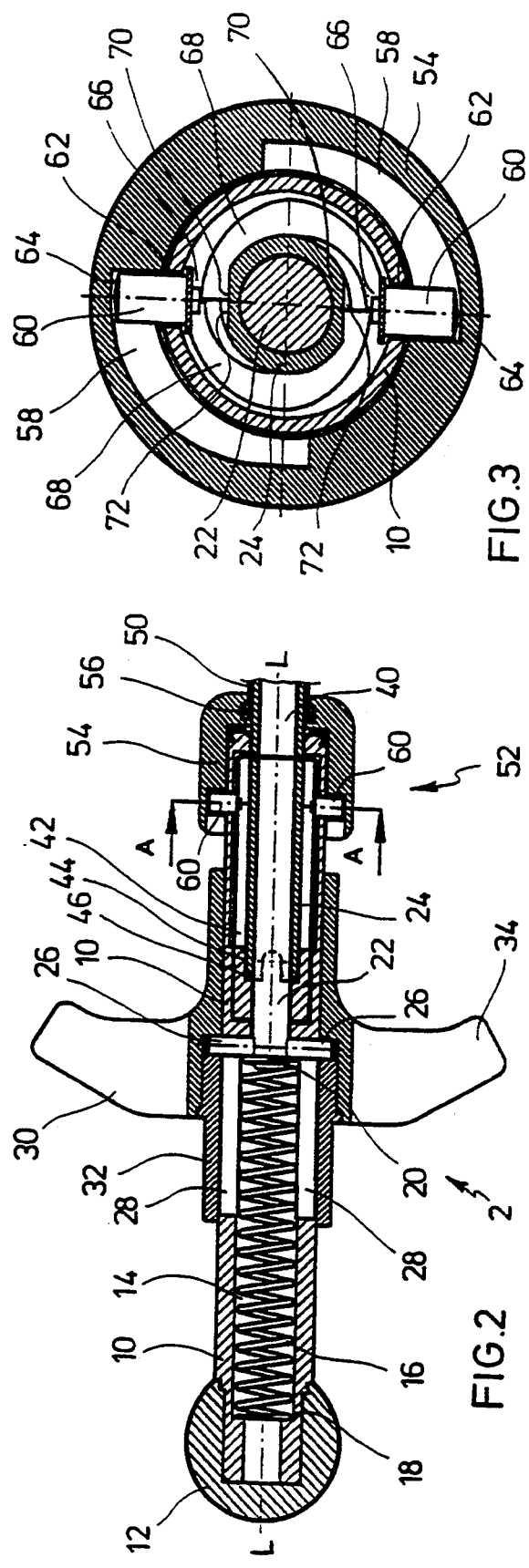

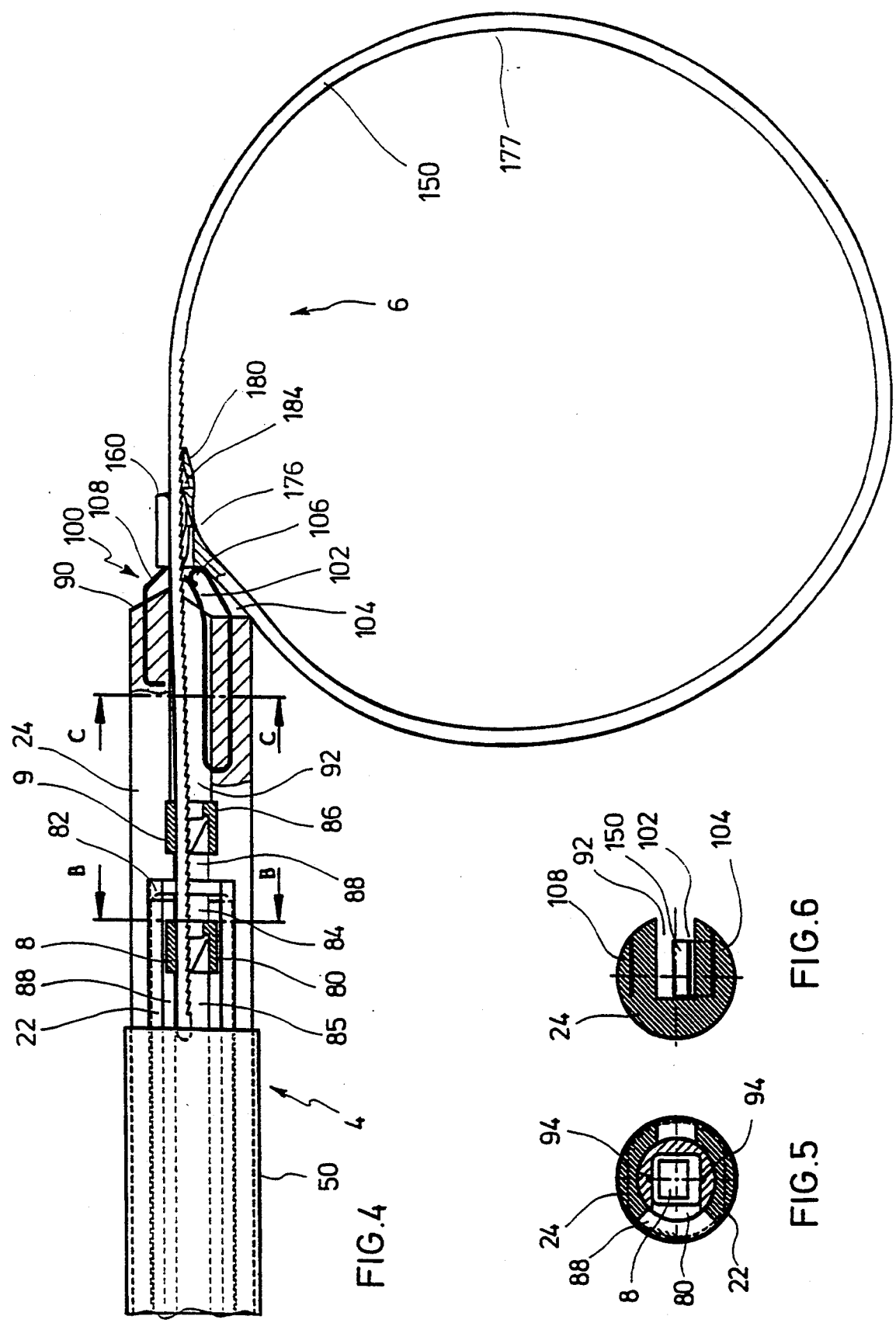

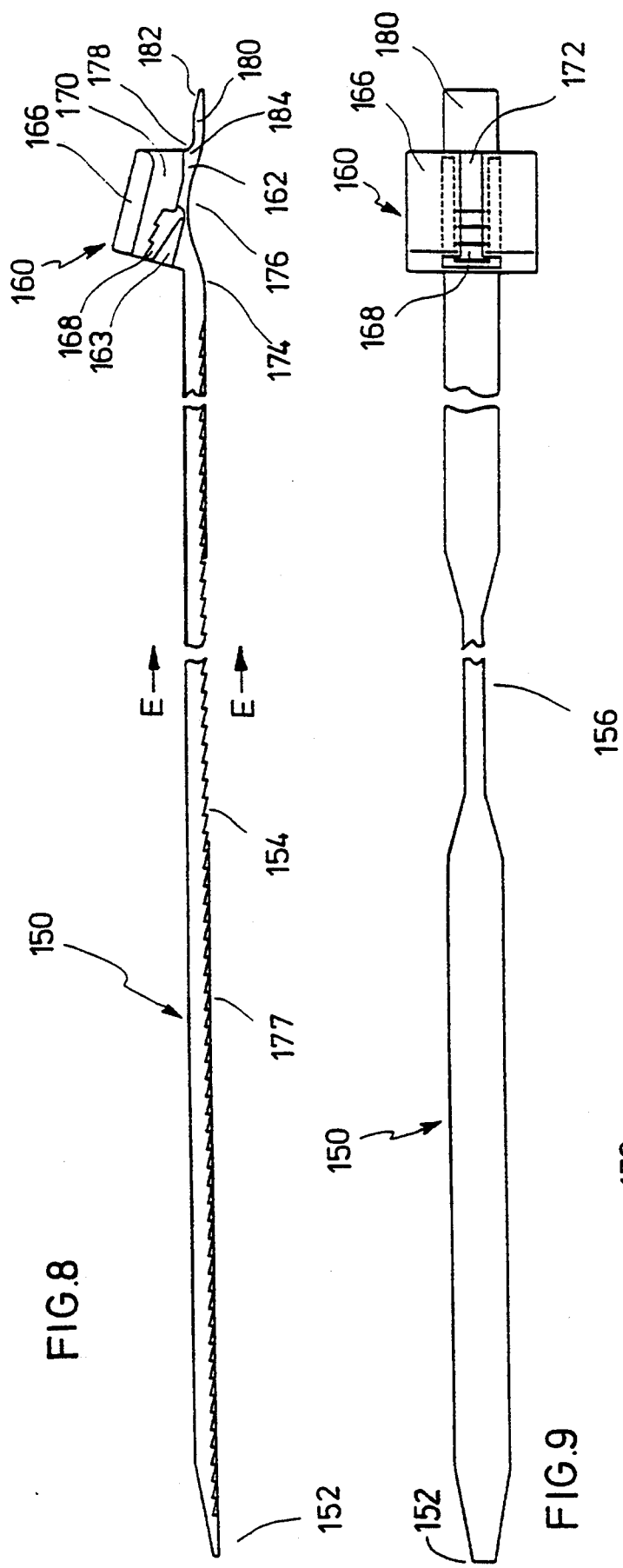
FIG. 8
FIG. 9
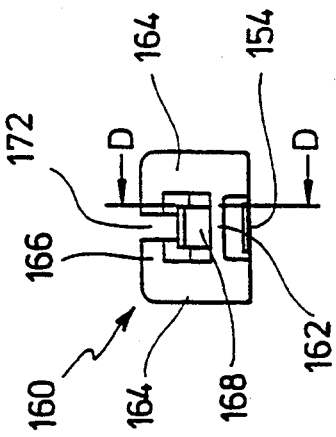
FIG. 10

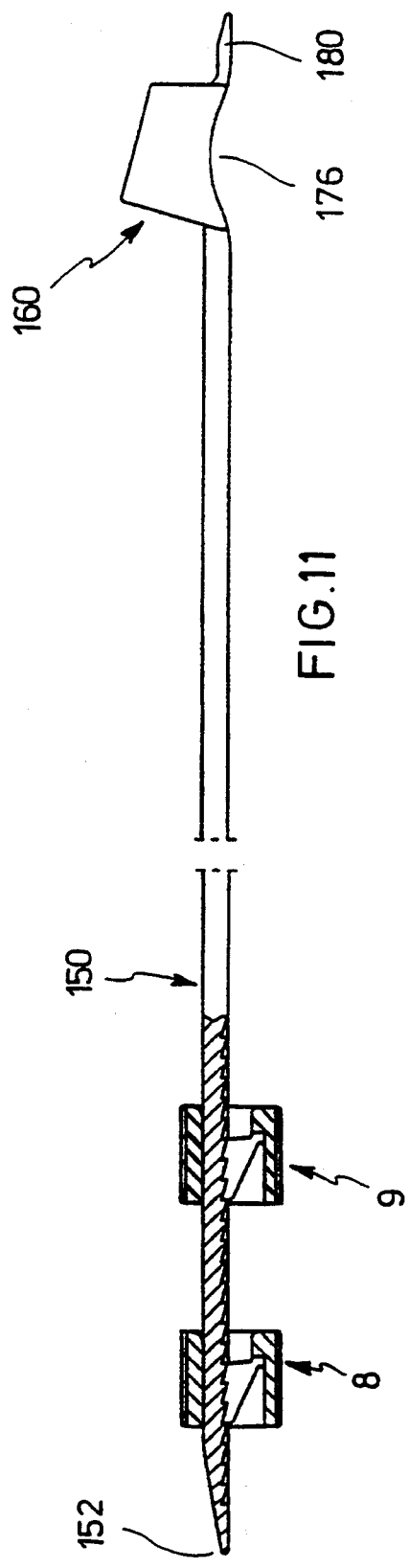
FIG.11
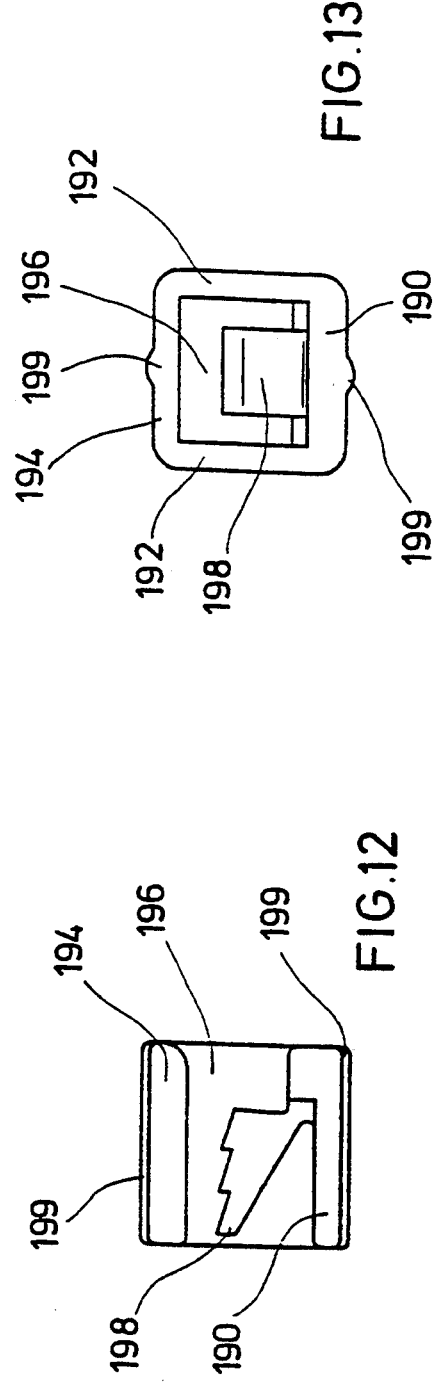
FIG.13
FIG.12

LIGATURE AND LIGATURE APPLYING ENDOSCOPIC INSTRUMENT

PRIORITY

This invention claims priority from German Application No. P4228909.2, filed Aug. 28, 1992, entitled "Endoscopic instrument for the application of ligature binders and ligature binder."

FIELD OF THE INVENTION

The invention relates to an endoscopic instrument for the application of ligatures, especially in the abdominal area, and to a ligature which can be applied using the endoscopic instrument described according to the invention.

BACKGROUND OF THE INVENTION

In modern minimally invasive surgery, instruments necessary for an operation are introduced into the abdominal cavity through one or several cannulae (trocar sleeves) and guided under the control of an endoscope, which has likewise been introduced into the abdominal cavity. Surgical areas are sometimes cared for by means of intraabdominal ligatures, for example by an Endoloop TM ligature with a slip knot. These are introduced with a tubular applicator into the area which is to be ligated, and are placed around the graspable stump of a hollow organ or of a bundle of vessels. The loop is pulled tightly outside the body, or closed with a ligature clip. The endoscopically monitored placement of such an endoligature loop calls for great manual dexterity and is also possible only with freely graspable vessel stumps. End-to-end anastomosis of hollow organs in laparoscopic operation techniques pose additional concerns. For instance, in open surgery, a purse-string suture must be applied if an end-to-end anastomosis is to be performed with a circular stapling device. Known from WO90/06725 is a laparoscopic instrument for the application of endoligatures and for the looping about of hollow organs, which instrument is introducible into the abdominal area through a cannula. This instrument has an instrument tube containing a ligature on the distal end of the headpiece. The headpiece is provide with a continuous channel which runs in the longitudinal direction of the instrument tube. A belt-like, loop-shaped continuation connects with the distal end of the headpiece. The free end of the continuation is grasped by the operator by means of an additional auxiliary aid, laid about the organ to be tied off and introduced into the channel. The free end of the belt-like continuation and the channel are provided with notched surfaces which correspond to each other. In the inside of the instrument tube, the free end can be grasped by a gripping tool, which tool is movable in the longitudinal direction, so that the ligature binder may be pulled tight. The notched surfaces prevent a release or loosening of the connection.

A drawback of this previously known laparoscopic instrument is that, upon introduction into the headpiece, the free end of the belt-like continuation forms an acute angle in the area where the belt-like continuation adjoins the headpiece. As a result, the shaped of the loop differs markedly from the ideally circular shape to be placed around the organ. It is awkward for the operator to have to pull the end of the actuation rod, which is coupled to the gripping tool, along the full length of the instrument tube through which the ligature binder is tightened.

SUMMARY OF THE INVENTION

The object of the invention is to provide an endoscopic instrument for the application of ligatures and an associated ligature which can be comfortably and safely handled by the operator, with which the ligature approaches a closed circular shape where it touches the looped vessel or organ.

To achieve this object, an endoscopic instrument for the application of ligatures and ligature are disclosed. A to-and-fro movement of an actuation part placed at the handle part, relative to the gripping part, causes a to-and-fro movement, of two ratchet heads relative to each other at the distal end of the instrument tube. The toothed ligature, it can be moved by the ratchet heads so that the ligature draws itself together.

The toothed end of a ligature designed according to the invention can be inserted into the two ratchet heads even before the introduction of the instrument through a cannula. The longitudinal slot in the counter-support of the headpiece permits the ligature and the headpiece to be brought together without having to thread the free end of the ligature through the headpiece. A consequence of this is that, in its closed form, the ligature corresponds largely to a circle.

In an advantageous design of the ligature, the base of the headpiece has on its underside a recess essentially in the form of a segment of a circle. The effect of this is that the inside of the ligature comes even closer to an circular shape, because now the headpiece, which is rigid, is also matched to a specific circular shape. By molding on a noselike continuation at the free end of the base zone of the headpiece, the displacement of the ligature in this zone can be compensated.

The use of the endoscopic instrument according to the invention in combination with the ligature according to the invention is made much easier if the ligature is pretensioned by preliminary treatment is such a way that it automatically rolls up out of the stretched shape into a curved shape. The headpiece comes to rest in the vicinity of the constricted zone of the binder. The ligature can then be stretched prior to the introduction of the instrument through the cannula, with the help of a longitudinally displaceable slide tube which is guided by the shaft of the instrument tube, and introduced in this form into the abdominal area. The slide tube is then pulled in a proximal direction, whereupon the ligature returns to its preformed curve and lays itself about the desired organ. The binder can then easily be introduced through the longitudinal slot in the counter-support of the headpiece with the help of a gripping tool which is. introduced into the abdominal area through another cannula. The shaped of the ligature is thus closed and can be made narrower by actuation of the gripping part of the laparoscopic instrument.

In an advantageous design of the endoscopic instrument according to the invention, a cutting device for cutting off the end-piece of the ligature is arranged at the distal end of the shaft. Upon actuation of the handle part, the closed ligature is first pulled in proximal direction until the headpiece lies against the distal end of the shaft. Only then does the ligature opening become narrower. The cutting device automatically severs the surplus free end of the ligature, which is now found in the inside of the endoscopic instrument. In this way, it is not necessary to introduce an additional cutting device through a separate cannula.

The two ratchet heads which are secured respectively at the actuation rod and at the shaft of the endoscopic instrument are preferably already positioned in the vicinity of the free end of the binder prior to use. They can be similar in structure to the headpiece of the ligature binder and made from the same material as the ligature binder, preferably from plastic.

The securing devices for the two ratchet heads are advantageously designed as openings at the actuation rod and at the shaft, respectively, of the endoscopic instrument, so that the ligature can easily be inserted in the instrument prior to the introduction of the instrument through the cannula.

During operation, parts of the endoscopic instrument can come into contact with blood or contaminated tissue. This particularly affects the two ratchet heads, which do not come directly into contact with tissue parts, but through which the binder part of the ligature is pulled. It is thus advantageous to supply the ratchet heads as disposable articles together with the ligature itself. Even the cutting device may come into contact with tissue, and can therefore be designed together with the shaft as a disposable article. On the other hand, the handle part and the actuation part, whose securing device for the ratchet head can be easily cleaned, and also the slide tube, are preferably used repeatedly and sterilized before every use.

The ligature according to the present invention can be used advantageously independent of the endoscopic instrument for the application of ligature binders according to the present invention, and optionally also without fitted ratchet heads.

DESCRIPTION OF THE DRAWINGS

The invention is described more preciously below with the help of a preferred embodiment.

The drawings show:

FIG. 1 an overall view, represented partially as longitudinal section, of the endoscopic instrument according to the invention, a portion of a closed ligature being visible at the distal end;

FIG. 2 a longitudinal section through the handle part and the coupling of the slide tube of the endoscopic instrument according to the invention;

FIG. 3 a cross-section along the line A—A from FIG. 2;

FIG. 4 a magnified longitudinal section through the distal zone of the instrument tube of the endoscopic instrument according to the invention, the slide tube being pulled back and an already closed ligature according to the invention with two ratchet heads being inserted;

FIG. 5 a cross-section along the line B—B from FIG. 4;

FIG. 6 a cross-section along the line C—C from FIG. 4;

FIG. 8 a longitudinal section along line D—D from FIG. 10 through a ligature according to the invention;

FIG. 9 a top view of the ligature according to the invention;

FIG. 10 a projection view of the ligature according to the invention along the arrows E from FIG. 8;

FIG. 11 a ligature according to the invention with two fitted ratchet heads in side view, the zone with the ratchet heads being shown in section;

FIG. 12 a longitudinal section through one of the ratchet heads; and

FIG. 13 a cross-section through one of the ratchet heads.

DETAILED DESCRIPTION OF THE INVENTION

Figure 7:
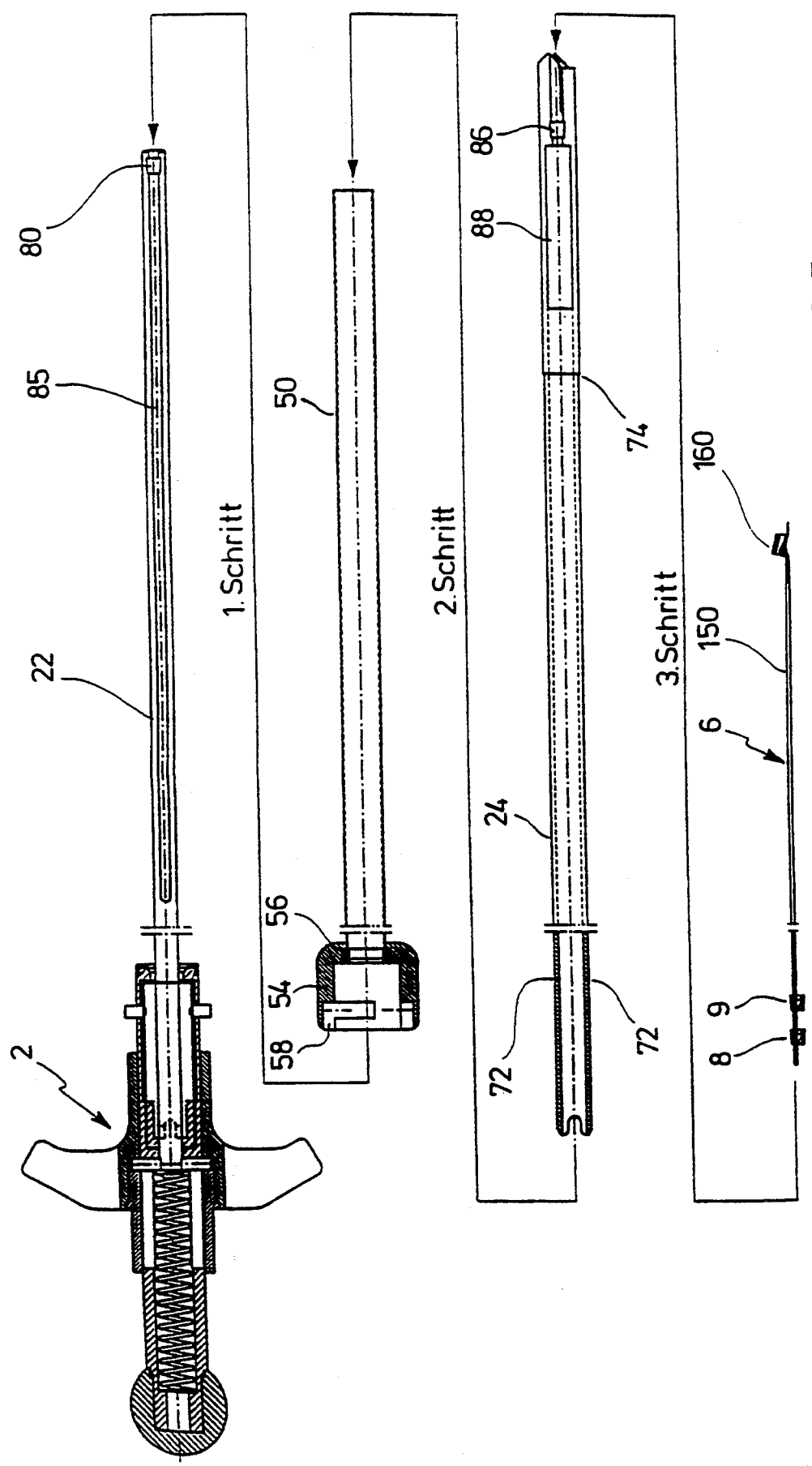
FIG. 7 a schematic representation which illustrates the assembly of the endoscopic instrument according to the invention.

FIG. 1 shows an overall view of an endoscopic instrument according to the present invention for the application of ligatures. An instrument tube 4 is placed onto a handle part 2, which has a base body 10 and an actuation part 30. The instrument tube 4 essentially comprises a cylindrical shaft 24, in which an actuation rod 22 is arranged in longitudinally displaceable manner. Upon longitudinal movement of the actuation part 30 relative to the base body 10, a first ratchet head 8 and a second ratchet head 9 at the distal end of the instrument tube 4 are pushed longitudinally relative to each other, as will be explained in more detail below, a ligature 6 located at the distal end of the instrument tube 4 is drawn via the ratchet heads 8 and 9.

As shown in FIG. 2, the handle part 2 contains the base body 10 (coarse hatching) and the actuation part 30 (fine hatching in the center zone). Located at the proximal end of the base body 10 is a knob 12 which lies preferably in the palm of the hand when the instrument is held. Arranged in longitudinal direction in an inner area 14 of the base body 10 is a compression spring 16 which lies with its proximal end against a projecting surface 18. The other end of the compression spring 16 engages at the proximal end 20 of the actuation rod 22, which is supported in longitudinally displaceable manner and guided in the essentially cylindrical shaft 24.

In the vicinity of its proximal end 20, the actuation rod 22 is connected to the actuation part 30 with the help of a pin 26. The pin 26 is guided by two longitudinal slots 28 in the housing of the base body 10. The longitudinal slots 28 limit the displacement range of the actuation part 30 and simultaneously make possible a rotation of the actuation part 30 relative to the base body 10. The pin 26 is housed between a proximal sleeve 32 and a gripping sleeve 34 which both form the actuation part 30 which is guided in longitudinally displaceable manner on the base body 10. The gripping sleeve 34 can be grasped by the fingers at its radially outwardly projecting zones, so that the handle part 2 as a whole lies in an ergonomically favorable manner in the operator's hand.

Arranged at the distal end of the handle part 2 is an aperture 40 through which the proximal end zone of the shaft 24 can be introduced into an anchorage space 42. The inserted shaft 24 lies with its proximal end 44 against an abutting surface 46.

Pushed over the shaft 24 is a slide tube 50 whose internal diameter is slightly greater than the external diameter of the shaft 24 and which is somewhat shorter than the shaft 24. The clamping part 54 of a coupling 52 is secured at the proximal end of the slide tube 50. Arranged in an annular groove of the clamping part 54 is a friction ring 56 which prevents slippage of the slide tube 50 once it has been pulled to a certain position along the shaft (and which simultaneously serves as a seal against gas losses during an endoscopic operation taking place under pressure). When the slide tube 50 is pushed forward to its maximum in distal direction, the friction ring 56 comes to rest against a projection 74 of the shaft 24 (see FIG. 7).

The coupling 52 serves on the one hand to lock the slide tube 50, which is advantage for the assembly of the endoscopic instrument, and on the other hand the shaft 24 is anchored in the base body 10 with its help. When the coupling 52 is unlocked, the shaft 24 is firmly connected to the base body 10, while the slide tube 50 can be displaced. Only when the coupling 52 is locked can the shaft 24 be fitted or removed. In order to achieve this function, the coupling 52 is designed as a bayonet catch.

To this end, the clamping part 54 is fitted with curved tracks 58 for guide pins 60, see FIG. 3. The guide pins 60 run through bores 62 in the housing of the base body 10 and are housed displaceable in their longitudinal, direction, i.e., transversely relative to the longitudinal axis L—L of the endoscopic instrument.

The outside ends 64 of the guide pins 60 lie against the curved tracks 58. Their insides ends 66 are coupled with flat, elastic securing clips 68 whose flattened ends 70 can engage in recesses 72 of the shaft 24, see also FIG. 2 and 3, the guide pins 60 are presses radially outwards by the elastic securing clips 68, the flattened ends 70 of the securing clips 68 engaging in the recesses 72 and thus locking the shaft 24. If, on the other hand, the clamping part 54 of the coupling 52 is rotated by 90 degrees, the guide pins 60 are presses radially inwards by the curves tracks 58, the flattened ends 70 of the securing clips 68 being lifted away from the recesses 72 and thus freeing the shaft 24, so that it can be inserted in or removed from the anchorage space 42. When the coupling 52 is in this position, the slide tube 50 is locked at the base body 10 (see also the representation of the clamping part 54 in FIG. 7), from which the course of the curved tracks 58 in longitudinal direction of the instrument can be observed.

FIG. 4 shows the distal end of the instrument tube 4 in detail. In it, the actuation rod 22 is pushed forward into its distal end position. Provided in the vicinity of its distal end 82 in the actuation rod 22 is a first opening 80 which is essentially square-shaped, see also FIG. 5. This first opening 80 serves to secure the first ratchet head 8 which is preferably designed as a component of the inserted ligature 6. A first lateral opening 84 runs from the first opening 80 as far as the distal end 82 of the actuation rod 22. In proximal direction, the actuation rod 22 is preferably provided with a longitudinal slit 85 which serves to accommodate the toothed end of the ligature 6 when the latter is drawn to its closed shape.

A second opening 86 in the vicinity of the distal end 90 of the shaft 24 serves to secure the second ratchet head 9. The second opening 86 is also essentially square-shaped and laterally accessible, and an opening 88 in the wall of the shaft 24 connects with it in proximal direction. The opening 88 is so dimensioned that the first opening 80 is accessible at least when the action rod 22 is pushed forward in distal direction, as shown in FIG. 4. A second lateral recess 92 runs in distal direction between the second opening 86 and the distal end 90 of the shaft 24. When the slide tube 50 is pulled back (as shown in FIG. 4), a ligature 6 in which the first ratchet head 8 and the second ratchet head 9 are fitted, can be pushed laterally into the actuation rod 22 and the shaft 24 prior to the introduction of the endoscopic instrument through a cannula. Due to the arrangement of the first opening 80, the first lateral recess 84, the opening 88, the second opening 86 and the second lateral recess 92, the whole distal, end of the instrument tube 4 is accessible from the side, see also FIGS. 5 and 6. In the longitudinal direction, the ratchet heads 8 and 9 are fixed respectively through the first opening 80 and the second opening 86. In order to prevent the ligature 6, from falling through openings 80, 86, the openings 80, 86 are preferably provided with longitudinal grooves 94 into which projections 199 at the ratchet heads 8, 9 engage (see FIG. 5 and FIG. 13).

A cutting device 100 is attached to the distal end 90 of the shaft 24. With the help of the cutting device 100 the end of ligature 6 located in the inside of the instrument tube 4, is cut off as soon as the ligature 6 applies a specific force against the looped organ. The cutting device 100 comprises a blade 102 and a pressure spring 104, which are designed in one piece and inserted from the side into a slot of the shaft 24, and another pressure spring 108, likewise inserted laterally into a slot, see FIG. 6. The cutting device 100 functions as follows: After the ligature 6 has been closed, as will be explained more preciously, its headpiece 160 initially lies before the distal end 90 of the shaft 24. The end of ligature 6 is now drawn into the inside of the instrument tube 4 with the help of the two ratchet heads 8, 9. The headpiece 160 moves towards the cutting device 100 until it comes to rest against a bent end part 106 of the pressure spring 104 and the end of the other pressure spring 108. As long as the ligature 6 still does not lie tightly around the looped organ, the headpiece 160 exerts no noteworthy force on the pressure springs 104, 108. However, as soon as the ligature 6 is tightly drawn, the force increases rapidly and the bent end part 106 of the pressure spring 104 deflects, pressing blade 102 upwards until the latter severs the ligature 6. The pressure force at the looped organ at which this happens depends on the elasticity constants of the pressure springs 104, 108.

FIGS. 8 to 10 show a ligature according to the present invention for use with the endoscopic instrument according to the invention for application of ligatures. An elongated, flexible binding part 150 is provided on one side (on the underside in the embodiment represented) with a toothing 154, each tooth having one steep and one flat flank in the embodiment. The free end 152 of the binding part 150 is preferably flattened in the direction of the thickness (see FIG. 8) and somewhat pointed in the direction of the width (see FIG. 9). The binding part 150 contains a constricted zone 156 of reduced width, see FIG. 9. In the embodiment represented, the toothing 154 in the constricted zone 156 extends over the complete width of the binding part 150.

The base zone 162 of the headpiece 160 connects with the opposite of the binding part 150. Two side zones 164 extend upwards from the base zone 162, and a counter-support 166, held by the side zones 164, is arranged opposite the base zone. Located on the upper side 163 of the base zone 162 is a pawl 168, pre-tensioned in the direction of the counter-support 166, which serves as a stop element. The pawl 168 is preferably molded in one piece to the base zone 162. The pawl 168 engages at the toothing 154 when the flexible binding part 150 is curved to produce a closed shape and is guided through the aperture 170 formed by the base zone 162, the side zones 164 and the counter-support 166. The toothing 154 and the pawl 168 are so designed with reference to their cooperation that a movement of the binding part 150 is possible only in the direction of an ever narrower closed shape of the ligature 6.

In order to close the ligature 6 so that it assumes a shape according to FIG. 4, it is not necessary to push the free end 152 of the binding part 150 through the aperture 170, but the constricted zone 156 can be introduced into the headpiece 160 through a longitudinal slot 172 in the counter-support 166. As soon as the ligature 6 is more narrowly closed, the constricted zone 56 no longer lies inside the headpiece 160, with the result that the ligature 6 cannot open.

The underside 174 of the base zone 162 has a recess 176 which is essentially in the form of a segment of a circle when seen in longitudinal direction. The curvature of the recess 176 is matched to a pre-set circular diameter, so that the inside 177 of the binding part can, in cooperating with the recess 176, assume a shape which approaches an ideal circular shape with the pre-set diameter.

A nose-like continuation 180, whose end 182 preferably flattened, connects with the free end 178 of the base zone 162. When the ligature 6 is closed, the nose-like continuation 180 lies against the inside 177 of the binding part 150 and thus compensates for the displacement 184, corresponding to the material thickness in the base zone 162, of the binding part 150 at the free end 178 of the base zone 162.

In the embodiment represented, the toothing 154 is attached to the underside of the binding part 150 which underside, after closure, forms the inside 177 of ligature 6. It is also possible to provide the toothing on the upper side if the stop element is attached to the counter-support 166, for example divided into two on both sides of the longitudinal slot 172, and is pre-tensioned onto the base zone 162.

FIG. 11 shows how the first ratchet head 8 and the second ratchet head 9 are fitted onto the binding part 150 in the vicinity of the free end 152. The ratchet heads 8, 9 preferably have the same structure, similar to the headpiece 160. They each have a base zone 190, two side zones 192 and a counter-support 194, but the latter is not provided with a longitudinal slot. The binding part 150 can be guided through the aperture 196 formed by these parts. The base zone 190 is provided with a pawl 198 which is pre-tensioned in the direction of the counter-support 194, and preferably designed in one piece with the base zone 190. In order to allow only a relative movement of the respective ratchet head 8, 9 onto the headpiece 160, the design of the pawl 198 is matched to the shape of the toothing of the binding part 150.

Molded onto the outside of the base zone 190 and/or of the counter-support 194 are projections 199, preferably running in longitudinal direction, which can engage the corresponding longitudinal grooves 94 of the first opening 80 and/or second opening 86 of the endoscopic instrument, see FIG. 13 and FIG. 5.

The ligature 6 is preferably manufactured in one piece from plastics material, for example polyamide. The separately fitted ratchet heads 8, 9 can be made from the same material as the ligature binder 6.

A pre-treatment is necessary if the ligature binder is to roll up automatically from a stretched shade, as represented in FIG. 8 or FIG. 11, into a curved shape, as shown in FIG. 4. It is possible, but expensive; to injection-mold a ligature into a curved shape with pre-set diameter. A stretched ligature which has been molded by conventional means is more easily brought into a curved shape with pre-set diameter by introducing the binding part 150 through the headpiece 160.

Initially, the ligature is placed in this state under tension. If it is now exposed to gamma radiation, for example to cobalt-60 radiation as is usual for sterilization, the gamma rays effect a repolymerization of the plastics material, so that once the irradiation has finished the curbed shape represents the relaxed state. The ligature 6 can accordingly be stretch only upon exertion of a force and automatically reverts to the curved shape with pre-set diameter, the headpiece 160 coming to rest in the vicinity of the constricted zone 156 of the binding part 150 when the ligature 6 is previously irradiated in this configuration. Instead of gamma irradiation, a ligature 6 wound into the curved shape can also be subject to a heat treatment (or "tempering"), which likewise results in the curved shape representing the relaxed state.

The use of the endoscopic instrument according to the invention for the application of ligature binders with the ligature binders according to the invention as per the described embodiment takes place as follows:

First, the instrument is assembled. FIG. 7 illustrates the individual steps required for assembly. In the first step, the slide tube 50 is pushed over the actuation rod 22, the latter already being firmly fitted at the actuation part 30 of the handle part 2. Through rotation of the clamping part 54 of the coupling 52 designed as a bayonet catch, the slide tube 50 is locked at the base body 10 of the handle part 2. Now, in the second step, the shaft 24 can be introduced through the aperture 40 into the anchorage space 42 of the base body 10. If the clamping part 54 is now released through a quarter rotation, the slide tube 50 can be pushed forward in distal direction; at the same time as the clamping part 54 is released, the shaft 24 is locked at the base body 10, as previously described. In the third step, a ligature according to the invention with two fitted ratchet heads 8, 9 is introduced laterally into the distal end if the instrument tube 4, in such a way that the first ratchet head 8 sits in the first opening 80 (at the actuation rod 22) and the second ratchet head 9 in the second opening 86 (at the shaft 24).

The slide tube 50 is now pushed distally to grasp the ligature 6, which has been pre-tensioned to produce a curved shape, and is stretched so that it lies full-length inside the slide tube 50.

The endoscopic instrument with the fitted ligature 6 is introduced, in the next step, through a cannula into the inside of the body, so that the distal end of the pushed-forward slide tube 50 is in the vicinity of the organ to be looped. This process is observed via an endoscopic optical device introduced through another cannula. The slide tube 50 is now gradually pulled proximally, the whole instrument optionally being pushed forward further inwards. The ligature 6 which is released in this way curves into its relaxed shape, laying itself around the organ which is to be looped, for example around a blood vessel or, where an end-to-end anastomosis is being established, around the shaft of the counter-support (anvil) of a circular stapler apparatus with drawn-up organ part. When the slide tube 50 is pulled far enough, the ligature 6 is present in curved shape, and the constricted zone 156 of its binding part 150 is located in the vicinity of the longitudinal slot 172 in the located in the vicinity of the longitudinal slot 172 in the counter-support 166 of the headpiece 160. With the help of a laparoscopic gripping instrument which has been introduced through another cannula, slot 172 and somewhat tightened, so that the constricted zone 156 no longer lies immediately in the vicinity of the longitudinal slot 172.

The operator now moves the actuation part 30 at the handle part 2 longitudinally in a cylindrical motion. If it is pulled in proximal direction, the first ratchet head 8 at the actuation rod 22 locks and takes the ligature 6 with it in proximal direction. In this direction of movement the binding part 150 can be pulled through the second ratchet head 9 at the shaft 24. When the actuation part 30 moves back in distal direction under the force of the compression spring 16, the second ratchet head 9 locks and prevents the ligature 6 from being displaced back into its original position. On the other hand, with this procedure the binding part 150 slides through the first ratchet head 8. In this way, the closed ligature 6 is positioned against the instrument until the headpiece 160 lies against the bent end part 106 and against the pressure spring 108 of the cutting device 100. Upon continuation of such movement of the handle part 2, the ligature 6 draws together until the cutting device 100 responds at a pre-set pressure force and severs the binding part 150, as previously described.

The instrument can now be pulled back out of the cannula. The end zone of the ligature 6 with the two ratchet heads 8, 9 is easily removed laterally from the instrument and can be discarded. The shaft 24, preferably designed as a disposable article, with the cutting device 100 is likewise removed, while the other parts of the instrument can re-used after cleaning and sterilization.

The ligature 6 according to the invention can also be used in applications in which the described endoscopic instrument is not used, as the design of the binding part 150 and of the headpiece 160 and also, where appropriate, its preformed curvature is desired.

What is claimed is:

1. Ligature comprising:
   an elongated, flexible binding part which is provided with a toothing on one side at least in the area of a free end thereof;
   a headpiece having an aperture with a base zone which connects with the other end of the binding part, with two side zones extending from the base zone, with a counter-support connected to said side zones and lying opposite the base zone and said counter-support having a stop element, the stop element engaging at the toothing when the binding part is curved to produce a closed shape and is guided through the said aperture; said side zones and counter-support of such aperture permitting only a movement of the toothing in the direction of an ever narrower closed shape;
   in that the binding part has a constricted zone; and
   in that counter-support is provided with a longitudinal slot through which the constricted zone of the binding part is introducible into the headpiece; and
   said ligature pretensioned by preliminary treatment in such a way that it automatically rolls up into a curved shape and said headpiece comes to rest in the vicinity of the constricted zone of the binding part.

2. Ligature according to claim 1, characterized in that the stop element is a pawl, pre-tensioned in the direction of the counter-support and molded in one piece onto the base zone on its upper side, which pawl is matched to the toothing of the binding part.

3. Ligature according to claim 1, characterized in that the base zone has on its underside a recess which is essentially in the form of a segment of a circle when seen in longitudinal direction.

4. Ligature according to claim 1 characterized in that the ligature is molded in one piece from plastics material.

5. Ligature according to claim 1, further comprising a first ratchet head and a second ratchet head as components of the ligature, said ratchet heads attached before their use in the vicinity of the free end of the binding part.

6. Ligature binder comprising:
   an elongated, flexible binding part which is provided with a toothing on one side at least in the area of its free end;
   a headpiece having an aperture with a base zone which connects with the other end of the binding part, with two side zones extending from the base zone, with a counter-support connected to said side zones and lying opposite the base zone and said counter-support having a stop element, the stop element engaging at the toothing when the binding part is curved to produce a closed shape and is guided through said apertures said side zones and counter-support of said aperture permitting only a movement of the toothing in the direction of an ever narrower closed shape,
   characterized in that:
   the binding part has a constricted zone, and
   the counter-support is provided with a longitudinal slot through which the constricted zone of the binding part is introducible into the headpiece; and
   said ligature is pre-tensioned to automatically roll up into a curved shape and said headpiece comes to rest in the vicinity of the constricted zone of the binding part.

7. Ligature according to claim 6, characterized in that the stop element is a pawl, pre-tensioned in the direction of the counter-support, molded on in one piece onto the base zone on its upper side, which pawl is matched to the toothing of the binding part.

8. Ligature binder according to claim 6, characterized in that a nose-shaped continuation is molded on at the free end of the base zone, which continuation lies against the inside of the binding part when the ligature is closed, in order thus to compensate for the displacement of the binding part at the free end of the base zone.

9. Ligature binder according to claim 6 characterized in that the ligature is molded in one piece from plastics material.

* * * * *